United States Patent
Eglauer et al.

(10) Patent No.: US 7,207,219 B2
(45) Date of Patent: Apr. 24, 2007

(54) ROD-SHAPED ELEMENT FOR LIQUID LEVEL DETECTION AND CORRESPONDING DEVICE FOR LIQUID LEVEL DETECTION

(75) Inventors: Heribert Eglauer, Berchtesgaden (DE); Gerhard Schlager, Hallein (AT); Uwe Kolb, Schönau (DE); Ulrich Schubert, München-Gräfeling (DE)

(73) Assignee: Tecan Trading AG, Männedorf (CH)

( * ) Notice: Subject to any disclaimer, the term of this patent is extended or adjusted under 35 U.S.C. 154(b) by 25 days.

(21) Appl. No.: 11/178,571

(22) Filed: Jul. 11, 2005

(65) Prior Publication Data

US 2006/0048570 A1 Mar. 9, 2006

(30) Foreign Application Priority Data

Sep. 6, 2004 (EP) .................................. 04021098
Jun. 22, 2005 (EP) .................................. 05105535

(51) Int. Cl.
*G01F 23/24* (2006.01)
*G01F 23/00* (2006.01)

(52) U.S. Cl. .................................. 73/304 R; 73/290 R
(58) Field of Classification Search .............. 73/304 R, 73/290 R
See application file for complete search history.

(56) References Cited

U.S. PATENT DOCUMENTS 3,373,351 A * 3/1968 Rak ........................... 324/449
6,513,377 B1 * 2/2003 Sassi et al. ................ 73/304 R
2004/0050861 A1 3/2004 Lisec et al.

FOREIGN PATENT DOCUMENTS

| DE | 29609222 | 5/1996 |
| DE | 29780268 | 5/1997 |
| EP | 0269837 | 10/1987 |
| EP | 0670497 | 2/1995 |

OTHER PUBLICATIONS

Eurpoean Search Report for EP Application 05105535.8.

* cited by examiner

*Primary Examiner*—Hezron Williams
*Assistant Examiner*—Rodney Frank
(74) *Attorney, Agent, or Firm*—Notaro & Michalos P.C.

(57) ABSTRACT

A metal rod-shaped element for a liquid detecting device is essentially cylindrical and has first and second ends. In at least one length, starting from the second end, the element has an isolating coating and an electrode strip is provided which extends along a longitudinal axis of the element. The electrode strip is not electrically connected to the element and the strip comprises a high impedance material. Two flattened sections are provided where the metal of the element lies openly. In a cross sectional view the electrode strip is situated between the two flattened sections. A first contact mechanism is provided in order to establish, in the range of the first end, an electrical contact to the rod-shaped element, and a second contact mechanism is provided in order to establish, within the range of the first end, an electrical contact to the electrode strip.

15 Claims, 7 Drawing Sheets

Bottom view

ROD-SHAPED ELEMENT FOR LIQUID LEVEL DETECTION AND CORRESPONDING DEVICE FOR LIQUID LEVEL DETECTION

FIELD OF THE INVENTION

The invention concerns rod-shaped elements, preferably cannulas or pipettes, for detecting a liquid level and corresponding devices for detecting a liquid level.

The present application claims the priority up of the European patent applications EP 04021098.1, filed on 6 Sep. 2004, and EP 05105535.8, filed on 22 Jun. 2005.

BACKGROUND OF THE INVENTION

There are numerous laboratory systems and medical, as well as pharmaceutical devices, in which it is important to determine the level in test tubes, titer plates and the like. Such a level determination is of importance particularly if it concerns the automation of measuring or test sequences.

A sample handler for liquids is known from the German utility model DE 29780368 U1. Metallic hollow needles are used in accordance with this utility model with one or two electrical conductors. The hollow needle is coated with an antiadhesive, electrically isolating layer inside and outside. The electrical conductors are designed in such a way that they have contact with the liquid only with a very small, non-isolated surface in order to be able to determine the immersing of the sample handler into the liquid.

A similarly constituted sample handler with level sensor is described in the German utility model DE 29609222 U1. This sample holder also comprises a hollow needle, which is coated with an antiadhesive, electrically isolating layer inside and outside. On this layer a conductive strip is applied.

The two sample handlers mentioned have the disadvantage that they do not allow for the making of a statement about the submergence of the sample handler in a liquid. The sample handlers permit recognition only of whether the sample handler has touched a liquid surface with its apex. In addition, the production is quite complex, since the isolating coating must be provided both on the inside and the outside of the hollow needle. Thus an application of the invention addressed by these two utility models on hollow needles with small inside diameter is particularly difficult.

Such a sample handler is thus not really suitable for the detection of the liquid level of small liquid quantities in small containers or buckets. Besides, no statement about the submergence of the sample handler can be made.

Another type of sample handler is described in the European patent application EP 670497 A1. This sample handler exhibits an inside and an exterior conductive tube, which are put into one another concentrically. The total structure is relatively complex and such sample handlers are probably expensive in the production.

In the European patent application EP 269837 A2 a sample handler is described, which comprises a non conductive tube on which two individual electrodes are fixed. This structure is also relatively complicated. In addition due to the complicated perimeter shape there is the danger of sample contamination, since drops can remain hanging on the sample handler and can thus be unintentionally transferred into another container.

Therefore it is an objective to provide an element for detecting a liquid level which is simple in the production and thin (in order to be able to work with this element even under restrained conditions, for example in arrays). In addition, an appropriate device is to be made available for the detection of a liquid level. Further, an exact statement about the submergence of the element is possible and the solution according to invention sample contamination.

These objectives are achieved according to invention by a rod-shaped element according to the claims, by a device with several rod-shaped elements according to the claims and by a device for determining a liquid level. Preferred embodiments are to be taken from the respective dependent claims.

BRIEF DESCRIPTION OF THE DRAWINGS

The system according to the invention and/or the method according to the invention are now described on the basis of schematic drawings, illustrating by way of example of the principles of the invention. The scope of the invention is not intended to be limited by these drawings in which.

DESCRIPTION OF THE PREFERRED EMBODIMENTS

In the following, several advantageous embodiments of the invention are described, said embodiments being exemplary embodiments. These cover different implementations of the entire invention, and building blocks as well as individual parts of the invention. Generally, the described building blocks and individual parts of the different embodiments can be combined, that is the building blocks and individual parts of individual embodiments can themselves be replaced by the building blocks and individual parts of other embodiments. The combinations thereby obtained may require minor adjustments which are well-known for a person skilled in the art and which are thus not further described; such adjustments may be necessary for the cooperating or interlinking of the building blocks and individual parts.

In connection with the present invention occasionally the expression rod-shaped element is being used. This expression is meant to cover cannulas, pipettes or pikes. The cannulas and pipettes are hollow inside, the pikes, however, may be solid, i.e. they are not hollow. Such pikes have only the function of a sensing probe and not the function of a pipette or a dispenser. Preferably, the rod-shaped elements are made from high-grade steel or precious metal, whereby platinum is particularly suitable.

Figure 1A:
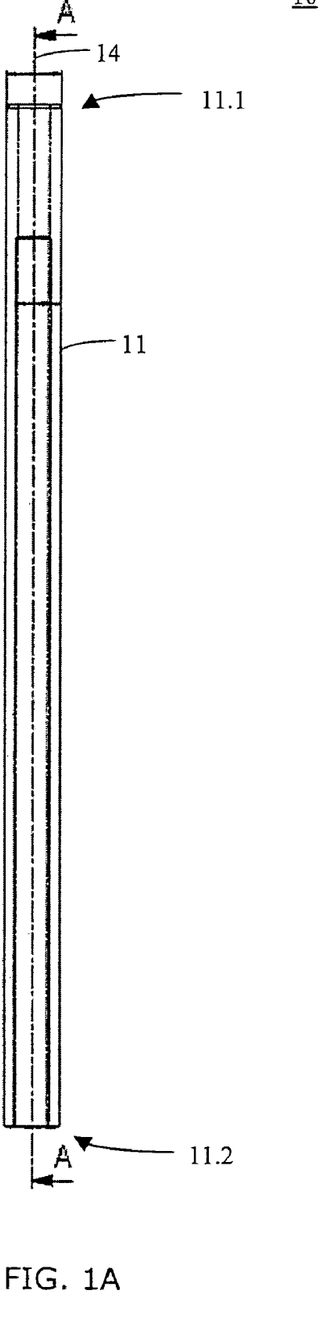
FIG. 1A shows a schematic side view of a first embodiment of the invention.
Figure 1B:
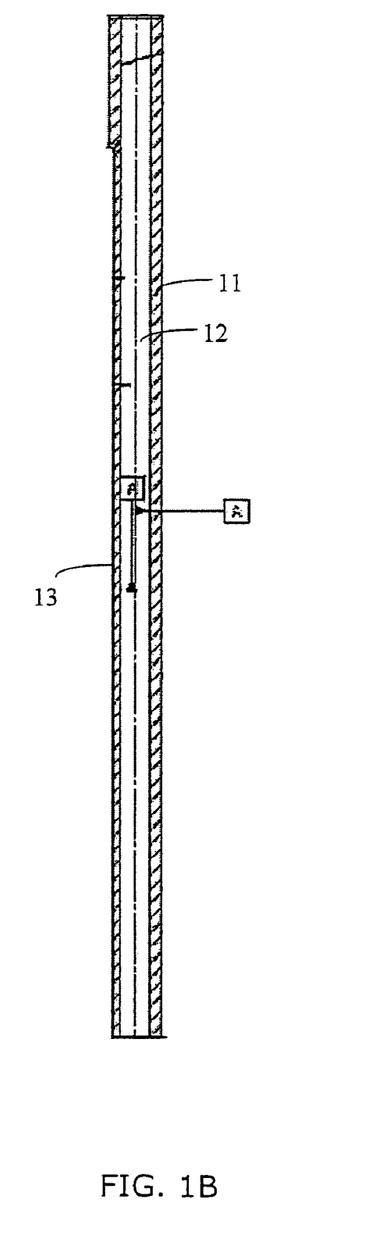
FIG. 1B shows a schematic cross-sectional view of the first embodiment of the invention.
Figure 1C:
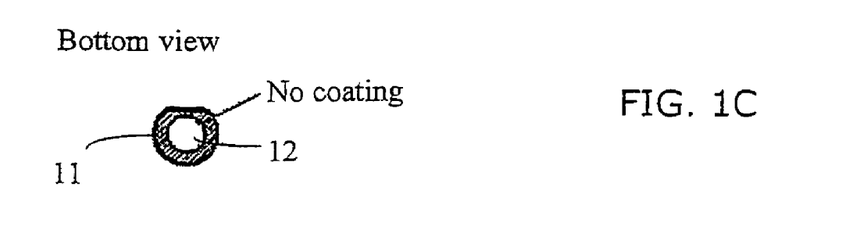
FIG. 1C shows a schematic view of the first embodiment of the invention from below.
Figure 1D:
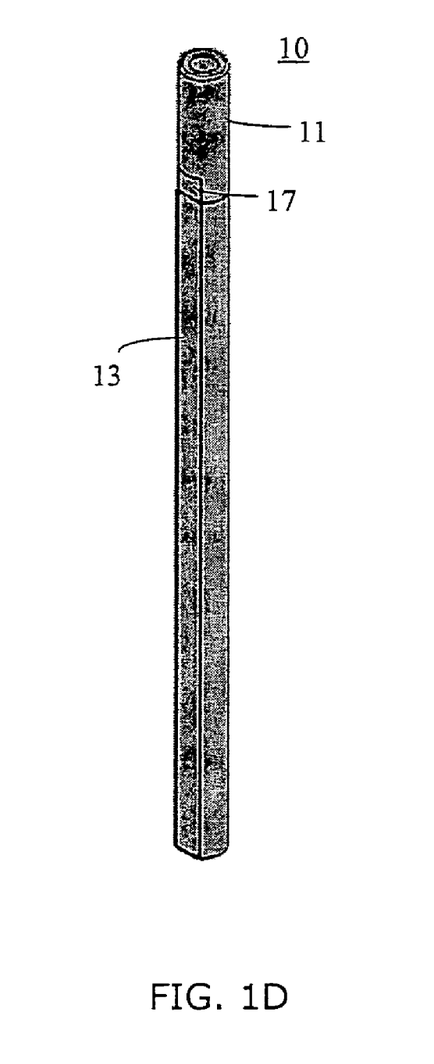
FIG. 1D shows a schematic, perspective view of the first embodiment of the invention.

In FIG. 1A–1B a first embodiment is shown, namely a rod-shaped element 10 having a first end 11.1 and a second end 11.2. The rod-shaped element 10 comprises an essentially cylindrical body 11 (e.g., a cannula or a pipette). There are at least two electrodes required, which are not electrically connected. First contact means are provided in order to establish in the range of the first end 11.1 an electrical contact to the first of the at least two electrodes, and second contact means are provided in order to establish in the range of the first end 11.1 an electrical contact to the second of the at least two electrodes. The rod-shaped elements 10 preferably are hollow inside (marked with 12), as already mentioned.

The rod-shaped element 10 is at least at one side 13 flattened. One of the electrodes (not visible in FIG. 1A to 1D) is realized on an intermediate layer 17, which is called isolating coating in the following.

Figure 2A:
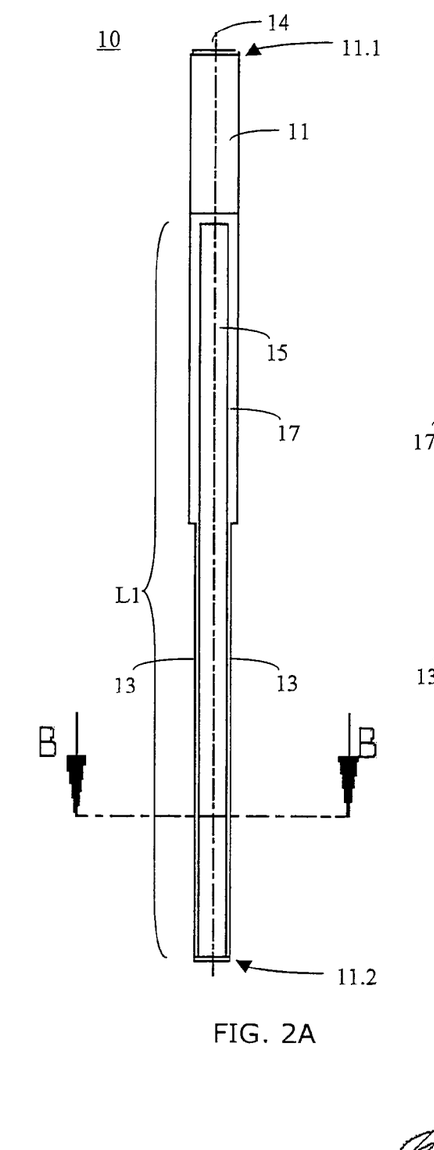
FIG. 2A shows a schematic side view, which shows a second embodiment of the invention.
Figure 2B:
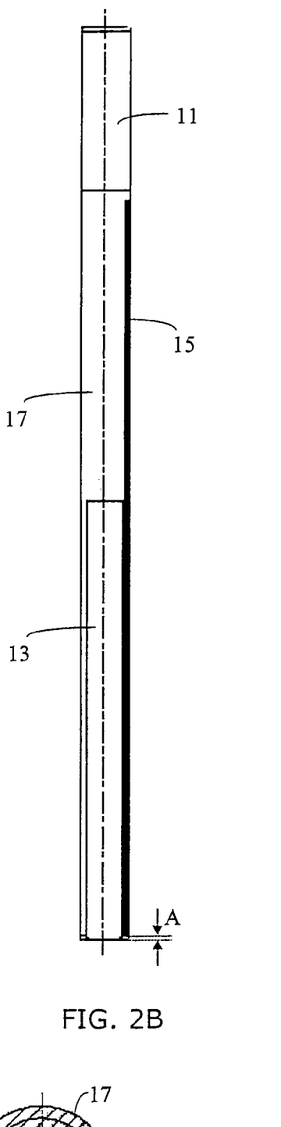
FIG. 2B shows a second schematic cross-sectional view of the second embodiment of the invention.
Figure 2C:
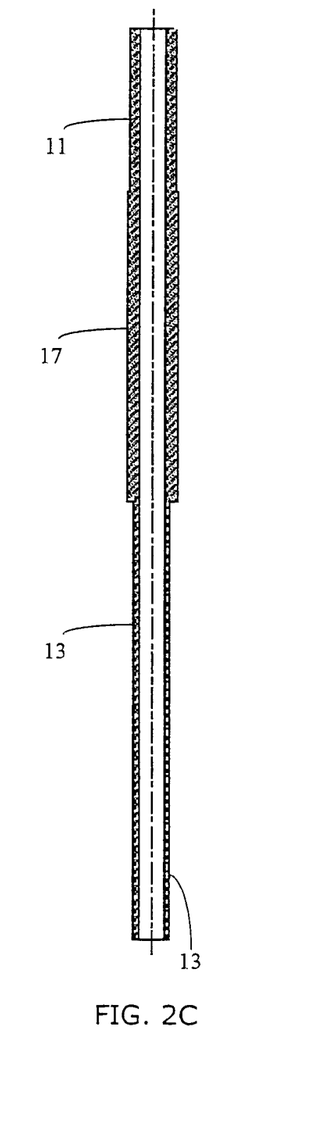
FIG. 2C shows a schematic cross-sectional view of the second embodiment of the invention.

In accordance with the invention the level is determined with an alternating voltage, which is now described in connection with a preferred embodiment. This particularly preferred embodiment is shown in the FIG. 2A to 2D. The rod-shaped element 10 is, as also shown in the FIGS. 1A to 1D, essentially cylindrically implemented and has a first upper end 11.1 as well as a second lower end 11.2. The rod-shaped element 10 is made of metal (precious metal or high-grade steel) and is at least in a length section L1, starting at the end 11.2, provided with an isolating coating 17. An electrode strip 15 is provided, which extends along a longitudinal axis 14 of the rod-shaped element 10, without being electrically connected to the rod-shaped element 10. This electrode strip 15 is formed from a high impedance (high resistivity) material. The electrode strip 15 represents a circular arc segment, as shown in FIG. 2C, which lies perpendicularly to the longitudinal axis 14.

The circular arc segment of the electrode strip 15 has preferably an electrode width, which is smaller than 25% of the total cylinder perimeter of the rod-shaped element 10. In other words expressed, the electrode strip 15 maximally occupies a quadrant of the cylinder cross section.

Unlike in the FIGS. 1A–1D, now two flattened length sections 13 are provided, which proceed from the second end 11.2 and extend at least a bit in the direction of the first end 11.1. In the cross section (see FIG. 2D) the two flattened length sections 13 confine the respective perimeter range of the cylindrical body 11 on both sides on which the electrode strip 15 is located. Further, first contact means are provided, in order to establish in the range of the first end 11.1 an electrical contact to the rod-shaped element 10. In addition, second contact means are provided, in order to establish in the range of the first end 11.1 an electrical contact to the electrode strip 15. These contact means are not shown in the FIG. 2A to 2D. In this embodiment the metallic body 11 of the rod-shaped element 10 serves as first electrode and the electrode strip 15 as the second electrode.

In case of the embodiment of the invention shown in the FIG. 2A–2D, the two flattened length sections 13 run essentially parallel to each other. In the cut B—B shown in FIG. 2D, the flattened length sections 13 represent flattenings of the circular cylinder cross section. Within the range of the flattened length sections 13 the coating 17 was removed and the material of the cylindrical body 11 was cleared away, which can be done for example by means of grinding. There are thus two exposed, lengthy ranges 13 of the metallic, cylindrical body 11 at both sides of the electrode strip 15. On the one hand one can with this structure increase the contact area between the liquid and the rod-shaped element 10 in comparison to conventional solutions. On the other hand the accuracy of the detection and the sensitivity are increased.

In a particularly preferred embodiment the coating 17 comprises a polymer material, which preferably is hydrophobic. Thus on the one hand a sample contamination can be prevented, since no drops remain hanging on the rod-shaped element 10. Primarily, however, the hydrophobic coating ensures that between the electrode strip 15 and the flattenings 13 running parallel to it no liquid drops or no liquid film does remain hanging. This is of special importance for the embodiments according to the invention, since they react very sensitively even to single drops, if these remain hanging between the electrode strip 15 and the flattenings 13 running in parallel.

A layer thickness of the coating 17 between 5 and 40 μm is particularly preferential. Particularly a layer thickness around approx. 30 μm has proved useful.

In accordance with the invention at least a further electrode can be provided, which preferably has an electrical contact area within the range of the first end 11.1.

The resistance can be determined at different submergences of the cannula and then the depth with respect to the liquid level can be computationally calculated. In accordance with the invention this can be done as follows. As soon as the rod-shaped element 10 dives into a conductive liquid, an electrically conductive connection (like a short-circuit) is formed between the electrode strip 15 serving as the first electrode and the conductive body 11 serving as the second electrode. One can determine now, for example by a resistance measurement or by observation of the voltage behavior, the moment when the rod-shaped element 10 touches the liquid. If one now continues to immerse the rod-shaped element 10 into the liquid, then the electrode strip 15 is horizontally short circuited with the metallic body 11 at the flattenings 13 further above. One can compare this behavior with a sliding potentiometer, where the center tap corresponds to the liquid level. If one pushes the center tap to the lower end of the sliding potentiometer (this corresponds to the case where the rod-shaped element 10 just dives into the conductive liquid), then the resistance is maximum. If one pushes the center tap of the sliding potentiometer upwards (towards the first end 11.1), then the resistance is reduced. This procedure is to be compared with the increasing immersing of the rod-shaped element 10 into the liquid. A high impedance resistive material is particularly suitable, since one thereby gets a good local resolution in z-direction.

If the element 10 is hollow, it can be used also for dispensing or aspirating liquid. At the same time this procedure can be monitored and/or controlled with the electrodes.

At the surface of a liquid to be detected there can be a small meniscus. The presence of a meniscus can be determined also via the resistance of the electrodes and the z-position of the rod-shaped element 10.

Figure 2D:
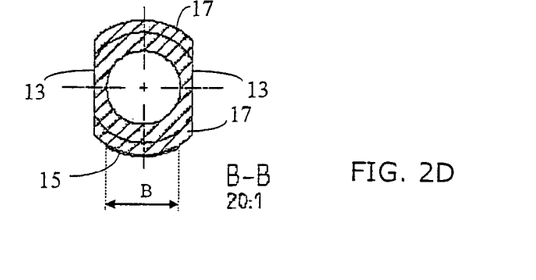
FIG. 2D shows a schematic, magnified (20:1) view of the cross section B—B of the second embodiment.
Figure 3A:
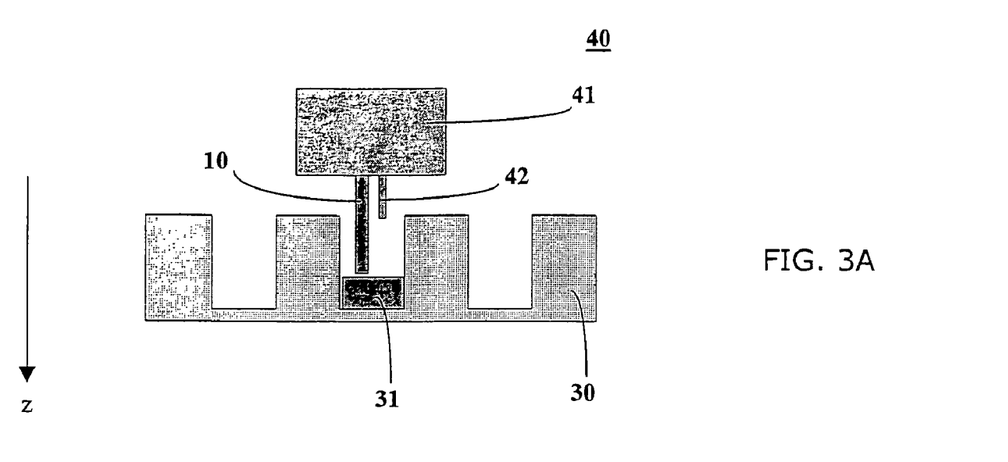
FIG. 3A shows a schematic representation, which shows one possible use (examination of the level) of an embodiment of the invention.

FIG. 3A shows a device 40, according to the invention, with a circuit 41, a cannula 10, one well 30 and a liquid 31. The cannula 10 is a cannula, which is implemented similarly to the rod-shaped element 10 shown in the FIG. 2A to 2D. If one moves the cannula 10 in z-direction and if the voltage between the electrodes, i.e. between the electrically conductive body 11 and the electrode strip 15 for example, is monitored (which can be done with the circuit 41), it can be determined very exactly on which level the liquid 31 is. This procedure is called LLD (LLD=liquid level detection).

With a rod-shaped element 10 according to invention and with an appropriate device 40 according to invention (which for example can be part of a washer) one can monitor the filling conditions of pipetted microtiter plates, which were filled outside of the device 40. The volumes are determined via the filling level within the pipetted microtiter plates and/or the z-heights of the rod-shaped elements 10 and the designated volumes of the pipetted microtiter plates manufacturer for certain filling levels with consideration of the tolerances.

Figure 3B:
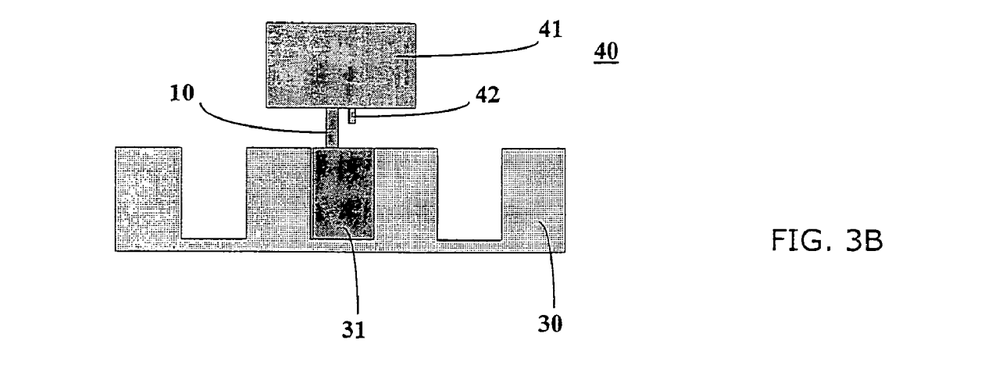
FIG. 3B shows a schematic representation, which shows a further use (process control) of an embodiment of the invention.

The device 40 can be used for washing wells 30, as suggested in FIG. 3B. Liquid 31 is injected by a dispensing needle 42 into the well 30 and the electrodes of the rod-shaped element 10 serve for the monitoring of the washing process.

By means of the invention an on-line process control of the overflow washing or washing can be realized. One can for example for a 96-well quasi continuously monitor between 50 and 400 µl and with a resolution of better than +/−20 µl, whether it is being dispensed and aspirated and/or whether the dispensing needle 42 or the suction needle 10 is clogged, as suggested in FIG. 3B.

Figure 3C:
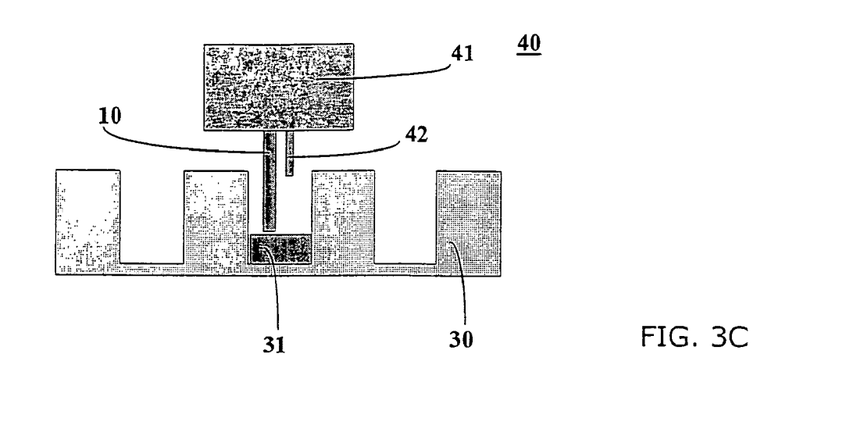
FIG. 3C shows a schematic representation, which shows a further use (examination of a suction procedure) of an embodiment of the invention.

The device 40 can be used also for sucking off wells 30, as suggested in FIG. 3C. Liquid 31 is sucked off the well 30 via the rod-shaped element 10 (which in this case serves as suction needle) and the electrodes of the rod-shaped element 10 serve for monitoring purposes to determine whether the level really reduces during sucking off.

With the device 40 according to the invention one can examine whether a suction procedure took place. Originally full wells 30 of microtiter plates will then be sucked off and in the microtiter plate it is examined with the device 40 whether all liquid was sucked off. Possibly in one well 30 remaining remainder volumes of the liquid can be detected with a high resolution by means of the device 40.

The following situations can occur for example in a washer. If at least one dispensing needles 42 is clogged, then the level in the appropriate well 30 sinks and the suction needle 10 sucks air. If at least the suction needles 10 should be clogged, then the level rises and the dispensing pump must be switched off immediately, in order to avoid an overflowing of the wells 30. If both the dispensing needle 42 and the suction needle 10 are clogged, then the suction needle 10 sucks air or the level rises. Also here the dispensing pump must be switched off. With a device according to invention 40 one can recognize such situations and intervene in time.

Figure 4A:
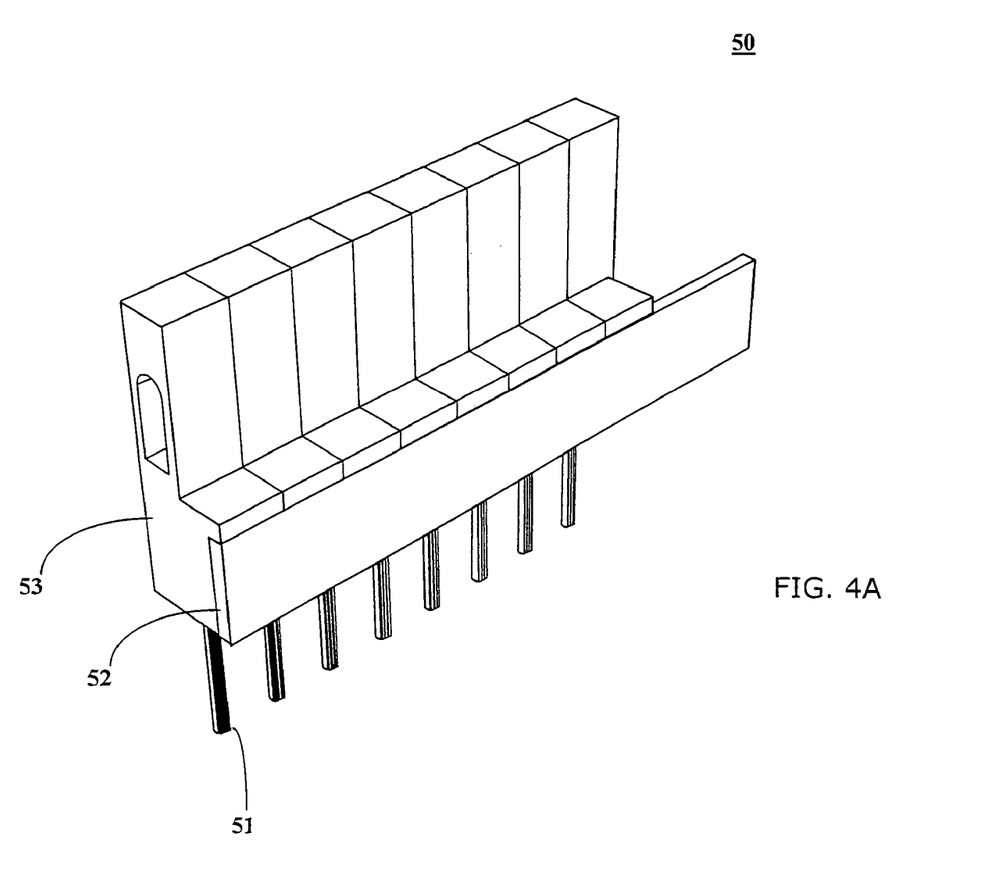
FIG. 4A shows a schematic, perspective view of a third embodiment of the invention.
Figures 4B, 4C:
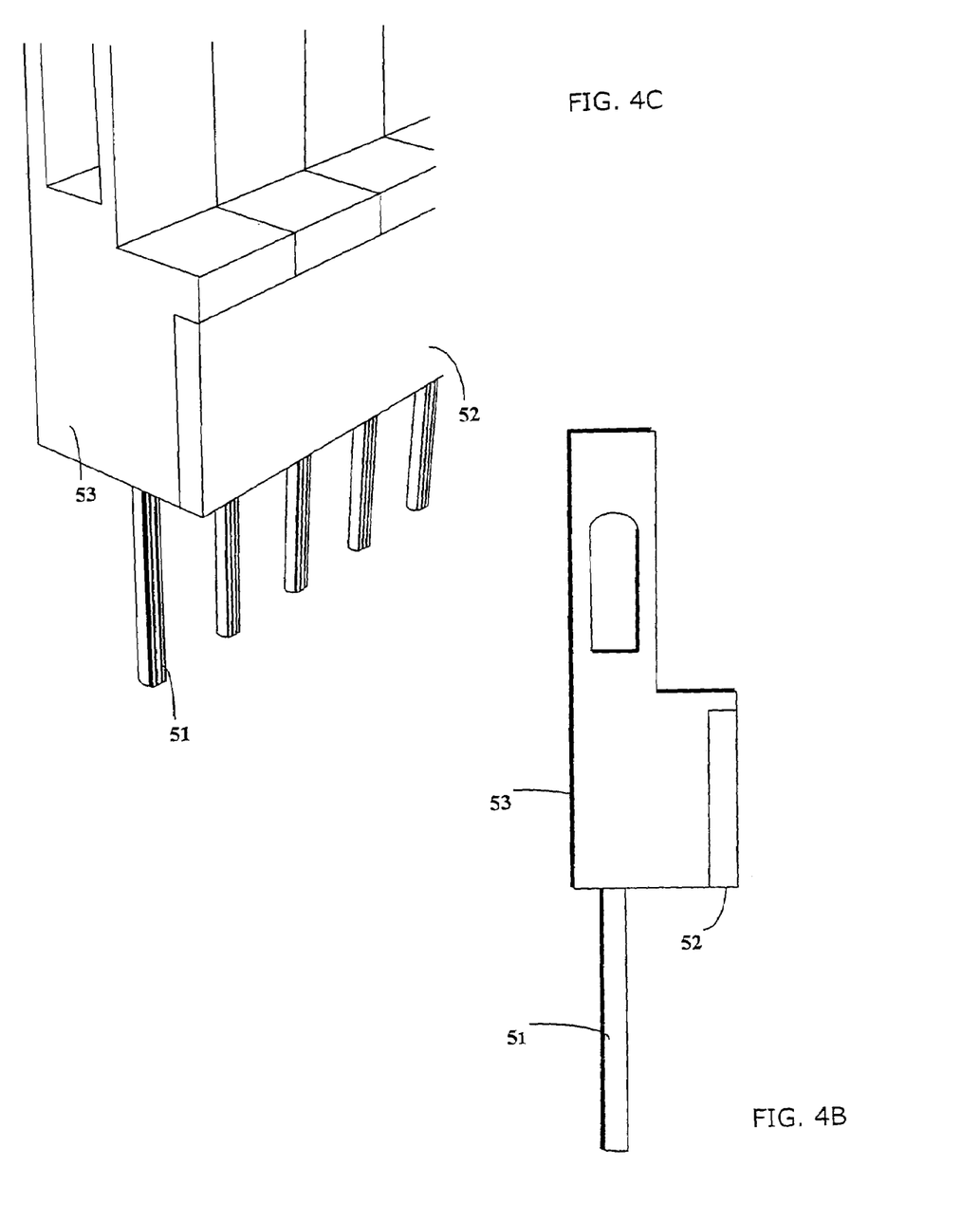
FIG. 4B shows a schematic perspective view of a part of the third embodiment of the invention.
FIG. 4C shows a schematic side view of the third embodiment of the invention.
Figure 4D:
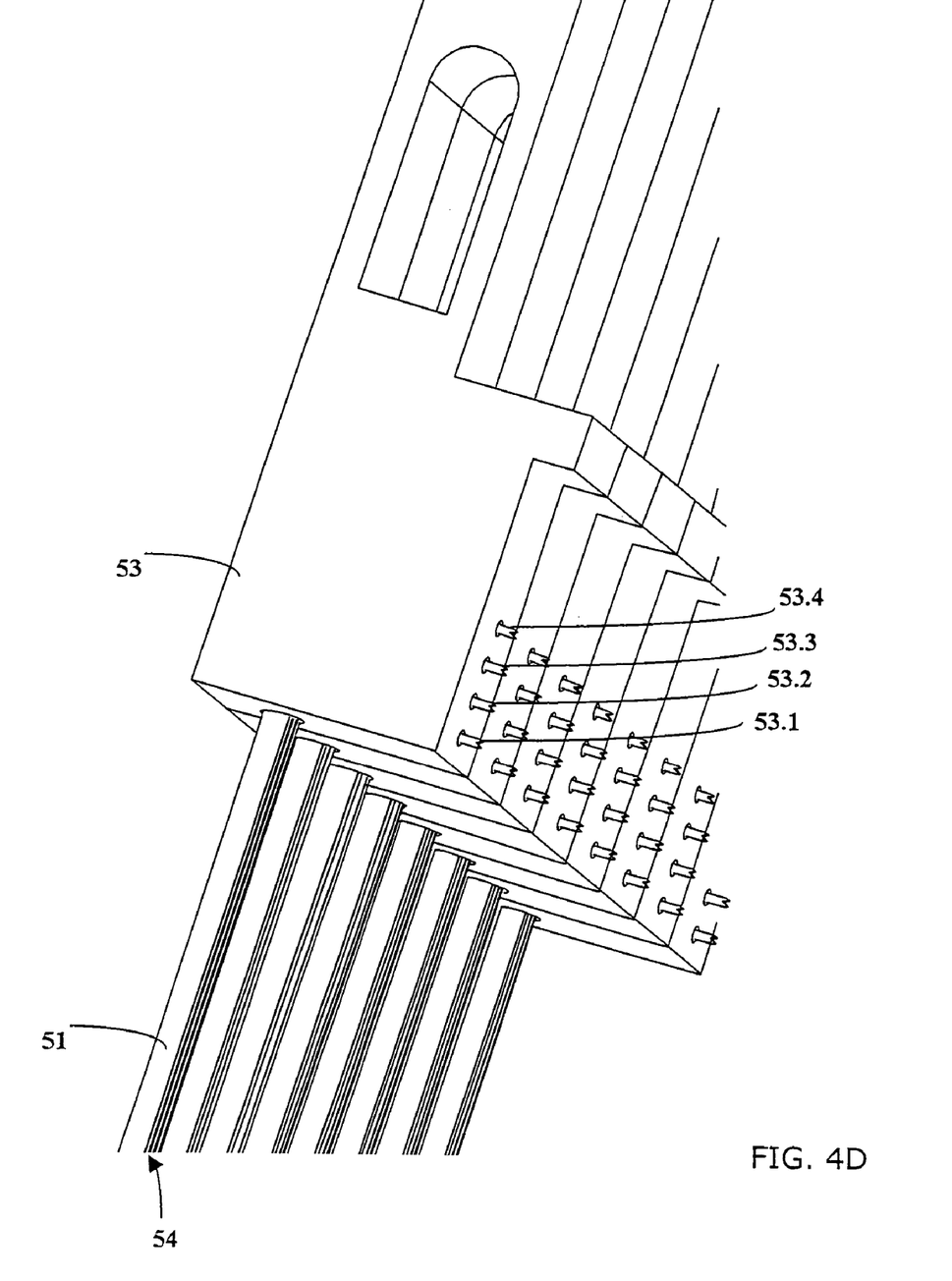
FIG. 4D shows a schematic view of the third embodiment of the invention.

In the FIGS. 4A–4D an array 50 for pipetting, and/or dispensing, and/or washing, and/or aspirating is shown. The array 50 comprises several rod-shaped elements 51, similar to the ones shown in the FIG. 1A–1D or 2A–2C. A circuit (electronics) is provided, which sits for example on a printed circuit board 52. The elements 51 are held in a housing 53. In FIG. 4C the flattened sides of the elements 51 with the electrode strip 15 are shown. FIG. 4D shows a situation without printed circuit board 52. There are contact pins 53.1, 53.2, 53.3 and 53.4 visible, which establish contacts between the circuit on the printed circuit board 52 and the electrodes, respectively the cannulas. In this context it is to be mentioned that the number of contact pins correlates with the number of electrodes to be contacted. If for instance 8 rod-shaped elements after FIG. 2A are used in an array after FIG. 4D, then one needs altogether 16 contact pins (2 pins per rod-shaped element 10).

The rod-shaped elements 10 can be manufactured in accordance with the invention relatively simply and economically. In addition they are very reliable and durable. They make a fast and very exact statement possible about the submergence in a liquid.

In a first manufacturing step the rod-shaped element, after it was cleaned and degreased, will be provided with the coating 17. Preferably, a polymer material is used as coating 17. Preferably, the coating 17 is laid on only on that section L1, which is dipped into liquid later and on which the electrode strip 15 will be. The polymer material preferably is hydrophobic and should be resistant to chemicals. After laying on the coating 17, the coating 17 is preferably burned at a temperature above 200 degrees Celsius (by annealing). Temperatures are particularly suitable around 300 degrees Celsius. It is important that this procedure runs without tension.

In a following step, a high impedance resistive material (preferably TiN) is preferably sputtered with a shadow mask. This procedure happens in a vacuum chamber of a sputtering system. If only one electrode strip 15 is used, then one can insert the rod-shaped element 10 into a slot of a shadow mask, which exposes only the length section L1 with a width, which is approximately as broad as the electrode width B of the later electrode strip 15. It is obvious that by the choice of the resistance material, in addition by geometry of the electrode strip 15 (layer thickness and electrode width), the resistance per unit of length can be changed.

The electrode strip 15 has a thickness, which amounts to between 20 nm and 500 nm.

Now the one or two flattenings are produced. This step is preferably carried out before sputtering, but it can also be carried out after the sputtering. The two flattenings can be manufactured by means of grinding. Preferably, the two flattened sections 13 run parallel to each other. As shown in FIG. 2D, the two flattened sections 13 limit that cylinder section, on which the electrode strip 15 comes to be. During the grinding both the coating 17 and a part of the metallic body 11 are removed.

The two flattened pages 13 do not have to run parallel. They can be arranged with respect to each other so that they define a certain angle, whereby care has to be taken that the wall thickness of the cylindrical part 11 does not become too thin.

Typically, the rod-shaped element 10 has a small radius in the transient area between the lateral surface of the cylinder and the front surface at the second end 11.2, i.e., at the lower end. In order to prevent that a short-circuit between the lower end of the electrode strip 15 and the metallically conductive body 11 of the rod-shaped element 10 exists, the electrode strip 15 is implemented in such a way, that there is a small distance A with respect to the lowest edge of the rod-shaped element 10. This distance A typically amounts to 0.1 mm (see FIG. 2B).

What is claimed is:

1. Rod-shaped element, which is essentially cylindrical and comprises a first end as well as a second end, whereby the rod-shaped element is made of metal, and
the rod-shaped element is provided with an isolating coating at least in a length section starting from the second end,
an electrode strip is provided that extends along a longitudinal axis of the rod-shaped element without being electrically connected to the rod-shaped element, whereby the electrode strip comprises a high impedance material and represents in a cross section, which lies perpendicularly to the longitudinal axis, a circular arc segment,
at least one flattened length section is provided which starts at the second end and where in the range of the at least one flattened length section the metal of the rod-shaped element is exposed, said electrode strip being positioned adjacent to the flattened length section,
first contact means are provided, in order to establish an electrical contact to the rod-shaped element,
second contact means are provided, in order to establish an electrical contact to the electrode strip.

2. Rod-shaped element according to claim 1, characterized in that it concerns a cannula, a pipette or a pike, which is hollow.

3. Rod-shaped element according to claim 2, characterized in that there are two flattened length sections being essentially parallel to each other and representing flattenings of the circular cylinder cross section if looked at in the cross section.

4. Rod-shaped element according to claim 1, characterized in that the electrode strip serves as first electrode and the rod-shaped element as second electrode of a resistance measuring bridge or a measuring circuit.

5. Rod-shaped element according to claim 4, characterized in that at least one of the two electrodes extends up to the second end.

6. Rod-shaped element according to claim 4, characterized in that the first electrode strip is applied on the coating, preferably by sputtering.

7. Rod-shaped element according to claim 1, characterized in that at least a further electrode is provided, which preferably has an electrical contact area within the range of said first end.

8. Rod-shaped element according to claim 4, characterized in that the coating comprises a polymer material, which preferably is hydrophobic.

9. Rod-shaped element according to claim 4, characterized in that the coating has a layer thickness between 5 and 40 µm, preferably about approx. 30 µm.

10. Rod-shaped element according to claim 4, characterized in that the circular arc segment of the electrode strip has an electrode width being smaller than 25% of the total cylinder perimeter of the rod-shaped element.

11. Rod-shaped element according to claim 4, characterized in that the electrode strip has a thickness, which amounts to between 20 nm and 500 nm.

12. Device with several rod-shaped elements according to claim 1, characterized in that the rod-shaped elements are arranged next to each other in a manifold head and carried by the manifold head, whereby at the manifold head electrical connections, which are each individually spring-mounted, are provided, in order to electrically contact each of the electrodes and each one of the rod-shaped element.

13. Device according to claim 12, characterized in that it concerns an array fpr pipetting, and/or dispensing, and/or washing, and/or aspiring.

14. Device for detecting a liquid level with one or more rod-shaped elements according to claim 1, characterized in that
a voltage supply is provided, in order to apply an alternating voltage between the electrode strip of a rod-shaped element and this rod-shaped element, and
a circuit is provided, which is designed for analysing current and/or voltage levels which are detectable between the electrode strip and the rod-shaped element.

15. Device according to claim 14, characterized in that the circuit comprises
a multiplexer in order to be able to evaluate the current and/or voltage levels of the different rod-shaped elements in an alternating fashion, and
an analog-digital converter which is situated downstream of the multiplexer.

* * * * *